United States Patent
Green et al.

(10) Patent No.: US 10,399,995 B2
(45) Date of Patent: Sep. 3, 2019

(54) 1,4-OXAZINES USEFUL AS SELECTIVE BACE1 INHIBITORS

(71) Applicant: Eli Lilly and Company, Indianapolis, IN (US)

(72) Inventors: Steven James Green, Indianapolis, IN (US); Erik James Hembre, II, Indianapolis, IN (US); Dustin James Mergott, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/323,827

(22) PCT Filed: Aug. 18, 2017

(86) PCT No.: PCT/US2017/047554
§ 371 (c)(1),
(2) Date: Feb. 7, 2019

(87) PCT Pub. No.: WO2018/039062
PCT Pub. Date: Mar. 1, 2018

(65) Prior Publication Data
US 2019/0161502 A1   May 30, 2019

Related U.S. Application Data

(60) Provisional application No. 62/380,007, filed on Aug. 26, 2016.

(51) Int. Cl.
| | | |
|---|---|---|
| *C07D 413/12* | (2006.01) | |
| *A61K 31/5377* | (2006.01) | |
| *C07D 513/04* | (2006.01) | |
| *A61P 25/28* | (2006.01) | |

(52) U.S. Cl.
CPC ............ *C07D 513/04* (2013.01); *A61P 25/28* (2018.01)

(58) Field of Classification Search
CPC ................ C07D 413/12; C07D 413/14; A61K 31/5377
USPC .......................................... 544/98; 514/228.8
See application file for complete search history.

(56) References Cited

U.S. PATENT DOCUMENTS

| | | | |
|---|---|---|---|
| 8,173,642 B2 | 5/2012 | Kobayashi et al. | |
| 8,207,164 B2 * | 6/2012 | Holzer ................ | C07D 265/30 514/233.2 |
| 8,653,067 B2 | 2/2014 | Kobayashi et al. | |
| 8,846,658 B2 | 9/2014 | Veenstra | |

FOREIGN PATENT DOCUMENTS

| | | |
|---|---|---|
| WO | 2011/009943 A1 | 1/2011 |
| WO | 2012/095451 A1 | 7/2012 |
| WO | 2012/095463 A1 | 7/2012 |

\* cited by examiner

*Primary Examiner* — Charanjit Aulakh
(74) *Attorney, Agent, or Firm* — Nelsen L Lentz

(57) ABSTRACT

The present invention provides a compound of Formula I: or a pharmaceutically acceptable salt thereof, useful as a BACE1 inhibitor.

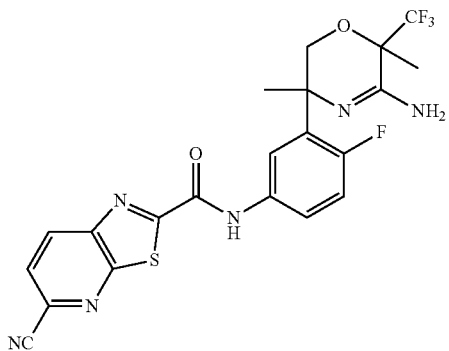

10 Claims, No Drawings

1,4-OXAZINES USEFUL AS SELECTIVE BACE1 INHIBITORS

The present invention relates to selective BACE1 inhibitors, to pharmaceutical compositions comprising the compounds, to methods of using the compounds to treat physiological disorders, and to intermediates and processes useful in the synthesis of the compounds.

The present invention is in the field of treatment of Alzheimer's disease and other diseases and disorders involving amyloid β (Abeta) peptide, a neurotoxic and highly aggregatory peptide segment of the amyloid precursor protein (APP). Alzheimer's disease is a devastating neurodegenerative disorder that affects millions of patients worldwide. In view of the currently approved agents on the market which afford only transient, symptomatic benefits to the patient rather than halting, slowing, or reversing the disease, there is a significant unmet need in the treatment of Alzheimer's disease.

Alzheimer's disease is characterized by the generation, aggregation, and deposition of Abeta in the brain. Complete or partial inhibition of β-secretase (β-site amyloid precursor protein-cleaving enzyme: BACE) has been shown to have a significant effect on plaque-related and plaque-dependent pathologies in mouse models suggesting that even small reductions in Abeta peptide levels might result in a long-term significant reduction in plaque burden and synaptic deficits, thus providing significant therapeutic benefits, particularly in the treatment of Alzheimer's disease. In addition, two homologs of BACE have been identified which are referred to as BACE1 and BACE2, and it is believed that BACE1 is the most clinically important to development of Alzheimer's disease. BACE is mainly expressed in the neurons while BACE2 has been shown to be expressed primarily in the periphery (See D. Oehlrich, *Bioorg. Med. Chem. Lett.*, 24, 2033-2045 (2014)). In addition, BACE2 may be important to pigmentation as it has been identified as playing a role in the processing of pigment cell-specific melanocyte protein (See L. Rochin. et al., *Proc. Natl. Acad. Sci. USA.* 110(26), 10658-10663 (2013)). BACE inhibitors with central nervous system (CNS) penetration, particularly inhibitors that are selective for BACE1 over BACE2 are desired to provide treatments for Abeta peptide-mediated disorders, such as Alzheimer's disease.

U.S. Pat. No. 8,846,658 discloses certain oxazine derivatives having BACE inhibitory activity. In addition, WO2012/095463 also discloses certain oxazine derivatives having BACE inhibitory activity.

The present invention provides certain novel compounds that are inhibitors of BACE1. In addition, the present invention provides certain novel compounds that are selective inhibitors of BACE1 over BACE2. Furthermore, the present invention provides certain novel compounds which penetrate the CNS. The present invention also provides certain novel compounds which have the potential for an improved side-effect profile, for example, through selective inhibition of BACE1 over BACE2.

Accordingly, the present invention provides a compound of Formula I:

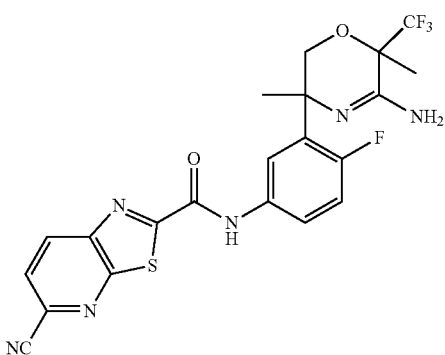

Formula I or a pharmaceutically acceptable salt thereof.

In addition, the present invention provides a compound of Formula Ia:

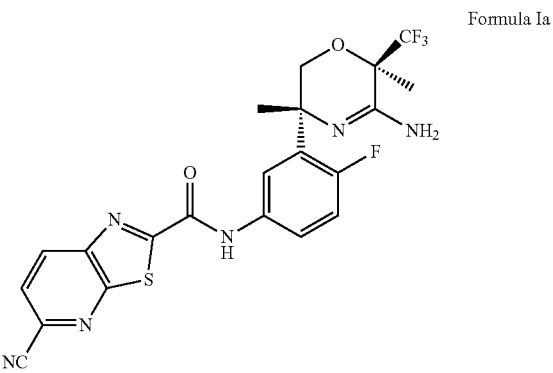 [SMILES: C[C@@]1(c2cc(NC(=O)c3nc4ccc(C#N)nc4s3)ccc2F)CO[C@@](C)(C(F)(F)F)C(N)=N1]

Formula Ia or a pharmaceutically acceptable salt thereof.

The present invention also provides a method of treating Alzheimer's disease in a patient, comprising administering to a patient in need of such treatment an effective amount of a compound of Formulas I or Ia, or a pharmaceutically acceptable salt thereof.

The present invention further provides a method of treating the progression of mild cognitive impairment to Alzheimer's disease in a patient, comprising administering to a patient in need of such treatment an effective amount of a compound of Formulas I or Ia, or a pharmaceutically acceptable salt thereof. The present invention also provides a method of inhibiting BACE in a patient, comprising administering to a patient in need of such treatment an effective amount of a compound of Formulas I or Ia. or a pharmaceutically acceptable salt thereof. The present invention also provides a method for inhibiting BACE-mediated cleavage of amyloid precursor protein in a patient, comprising administering to a patient in need of such treatment an effective amount of a compound of Formulas I or Ia, or a pharmaceutically acceptable salt thereof. The invention further provides a method for inhibiting production of Abeta peptide in a patient, comprising administering to a patient in need of such treatment an effective amount of a compound of Formulas I or Ia, or a pharmaceutically acceptable salt thereof.

Furthermore, this invention provides a compound of Formulas I or Ia, or a pharmaceutically acceptable salt thereof for use in therapy, in particular for the treatment of Alzheimer's disease or for preventing the progression of mild cognitive impairment to Alzheimer's disease. Even furthermore, this invention provides the use of a compound of Formulas I or Ia, or a pharmaceutically acceptable salt thereof, for the manufacture of a medicament for the treatment of Alzheimer's disease.

The invention further provides a pharmaceutical composition, comprising a compound of Formulas I or Ia, or a pharmaceutically acceptable salt thereof, with one or more pharmaceutically acceptable carriers, diluents, or excipients. The invention further provides a process for preparing a pharmaceutical composition, comprising admixing a compound of Formulas I or Ia, or a pharmaceutically acceptable salt thereof, with one or more pharmaceutically acceptable carriers, diluents, or excipients. This invention also encompasses novel intermediates and processes for the synthesis of the compounds of Formulas I and Ia.

Mild cognitive impairment has been defined as a potential prodromal phase of dementia associated with Alzheimer's disease based on clinical presentation and on progression of patients exhibiting mild cognitive impairment to Alzheimer's dementia over time. (Morris, et al., *Arch. Neurol.*, 58, 397-405 (2001); Petersen, et al., *Arch. Neurol.*, 56, 303-308 (1999)). The term "preventing the progression of mild cognitive impairment to Alzheimer's disease" includes restraining, slowing, stopping, or reversing the progression of mild cognitive impairment to Alzheimer's disease in a patient.

As used herein, the terms "treating" or "to treat" includes restraining, slowing, stopping, or reversing the progression or severity of an existing symptom or disorder.

As used herein, the term "patient" refers to a human.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be readily determined by one skilled in the art using known techniques and by observing results obtained under analogous circumstances. In determining the effective amount for a patient, a number of factors are considered by one skilled in the art, including, but not limited to: the patient's size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of the present invention are generally effective over a wide dosage range. For example, dosages per day normally fall within the range of about 0.01 to about 20 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The compounds of the present invention are preferably formulated as pharmaceutical compositions administered by any route which makes the compound bioavailable, including oral and transdermal routes. Most preferably, such compositions are for oral administration. Such pharmaceutical compositions and processes for preparing same are well known in the art. (See, e.g., Remington: The Science and Practice of Pharmacy, L. V. Allen, Editor, $22^{nd}$ Edition, Pharmaceutical Press, 2012).

The compounds of Formulas I and Ia, or pharmaceutically acceptable salts thereof are particularly useful in the treatment methods of the invention, but certain groups, substituents, and configurations are preferred. The following paragraphs describe such preferred groups, substituents, and configurations. It will be understood that these preferences are applicable both to the treatment methods and to the new compounds of the invention.

The compound of Formula Ia wherein the methyl at position 3 is in the cis configuration relative to the trifluoromethyl at position 6 on the oxazine ring is preferred as depicted in Scheme A:

Scheme A

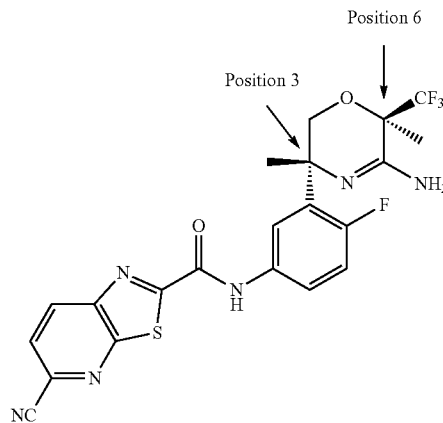

Formula Ia

Although the present invention contemplates all individual enantiomers and diasteromers, as well as mixtures of the enantiomers of said compounds, including racemates, the compound with the absolute configuration as set forth below is particularly preferred:

N-[3-[(3R,6R)-5-amino-3,6-dimethyl-6-(trifluoromethyl)-2H-1,4-oxazin-3-yl]-4-fluoro-phenyl]-5-cyano-thiazolo[5,4-b]pyridine-2-carboxamide, and the pharmaceutically acceptable salts thereof.

One of ordinary skill in the art will appreciate that compounds of the invention can exist in tautomeric forms, as depicted below in Scheme B. When any reference in this application to one of the specific tautomers of the compounds of the invention is given, it is understood to encompass both tautomeric forms and all mixtures thereof.

Scheme B

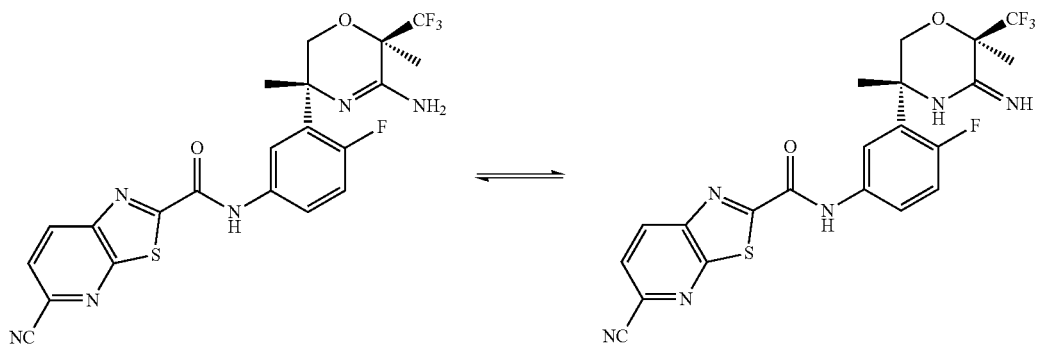

Additionally, certain intermediates described in the following preparations may contain one or more nitrogen protecting groups. It is understood that protecting groups may be varied as appreciated by one of skill in the art depending on the particular reaction conditions and the particular transformations to be performed. The protection and deprotection conditions are well known to the skilled artisan and are described in the literature (See for example "Greene s *Protective Groups in Organic Synthesis*", Fourth Edition, by Peter G. M. Wuts and Theodora W. Greene, John Wiley and Sons, Inc. 2007).

Individual isomers, enantiomers, and diastereomers may be separated or resolved by one of ordinary skill in the art at any convenient point in the synthesis of compounds of the invention, by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen," *Stereochemistry of Organic Compounds*", Wiley-Interscience, 1994).

A pharmaceutically acceptable salt of the compounds of the invention, such as a hydrochloride salt, can be formed, for example, by reaction of an appropriate free base of a compound of the invention, an appropriate pharmaceutically acceptable acid such as hydrochloric acid in a suitable solvent such as diethyl ether under standard conditions well known in the art. Additionally, the formation of such salts can occur simultaneously upon deprotection of a nitrogen protecting group. The formation of such salts is well known and appreciated in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000): and Berge, S. M., et al., "Pharmaceutical Salts," *Journal of Pharmaceutical Sciences*, 66: 1-19, (1977).

Certain abbreviations are defined as follows: "APP" refers to amyloid precursor protein; "ATCC" refers to American Type Culture collection; "BSA" refers to Bovine Serum Albumin; "cDNA" refers to complementary deoxyribonucleic acid; "CNS" refers to central nervous system: "DCM" refers to dichloromethane; "(DHQ)₂PHAL" refers to hydroquinine 1,4-phthalazinediyl diether; "DMSO" refers to dimethyl sulfoxide; "EBSS" refers to Earle's Balances Salt Solution; "ELISA" refers to enzyme-linked immunosorbent assay; "EtOAc" refers to ethyl acetate: "F12" refers to Ham's F12 medium: "FBS" refers to Fetal Bovine Serum: "Fc" refers to fragment crystallizable; "FRET" refers to fluorescence resonance energy transfer; "HEK" refers to human embryonic kidney; "IC$_{50}$" refers to the concentration of an agent that produces 50% of the maximal inhibitory response possible for that agent; "IgG$_1$" refers to immunoglobulin-like domain Fc-gamma receptor; "MEM" refers to Minimum Essential Medium; "MeOH" refers to methanol or methyl alcohol: "MTBE" refers to tert-butyl methyl ether; "PBS" refers to phosphate buffered saline: "PDAPP" refers to platelet derived amyloid precursor protein; "RFU" refers to relative fluorescence unit; "RT-PCR" refers to reverse transcription polymerase chain reaction: "SDS-PAGE" refers to sodium dodecyl sulfate polyacrylamide gel electrophoresis; "SCX" refers to strong cation exchange: "tBuXphos" refers to 2-di-tert-butylphosphino-2',4',6'-triisopropylbiphenyl; "tBuXphos precatalyst generation 3" refers to [(2-di-tert-butylphosphino-2',4',6'-triisopropyl-1,1'-biphenyl)-2-(2'-amino-1,1'-biphenyl)] palladium (II) methanesulfonate; "THF" refers to tetrahydrofuran; "TMEM" refers to transmembrane protein;

The compounds of the present invention, or salts thereof, may be prepared by a variety of procedures known to one of ordinary skill in the art, some of which are illustrated in the schemes, preparations, and examples below. One of ordinary skill in the art recognizes that the specific synthetic steps for each of the routes described may be combined in different ways, or in conjunction with steps from different schemes, to prepare compounds of the invention, or salts thereof. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. For example, certain starting materials may be in a manner analogous to procedures set forth in US2011/0021520 prepared as indicated in the preparations below. Without limiting the scope of the invention, the following schemes, preparations, and examples are provided to further illustrate the invention.

Scheme 1

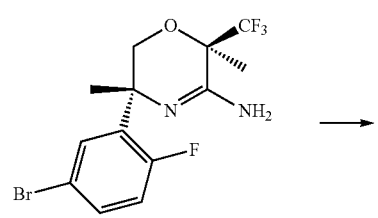

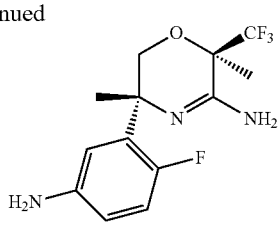

In Scheme 1, the 5-bromo-2-fluoro-phenyl substituted oxazine can be converted to an aniline under conditions well known in the art. For example, cuprous iodide, an inorganic base such as potassium carbonate, L-hydroxyproline, and a nitrogen source of ammonia in water are combined under microwave conditions at a temperature of about 100° C. to give the corresponding aniline.

Scheme 2

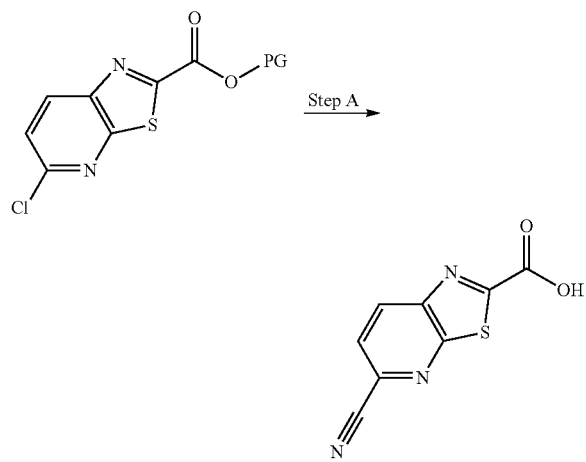

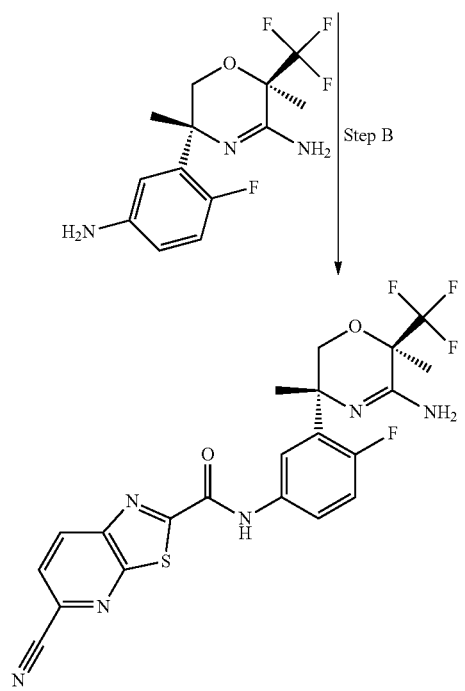

Formula Ia

In Scheme 2, a compound of Formula Ia can be prepared by acylation of the aniline from Scheme 1, with an acid chloride prepared in situ from the corresponding carboxylic acid. For example, in step A, the protected acid of 5-chlorothiazolo[5,4-b]pyridine-2-carboxylate can be converted to a protected acid of 5-cyano[1,3]thiazolo[5,4-b]pyridine-2-carboxylate in a solvent such as 1,4-dioxane using an inorganic base such as an aqueous solution of potassium acetate and a cyano source such as potassium ferrocyanide trihydrate, a precatalyst generation with tBuXphos precatalyst generation 3 and a catalyst such as tBuXphos. The mixture can be heated to about 90° C. and the cyano derivative isolated by work-up with an organic extraction in a solvent such as EtOAc and chromatography purification. The cyano derivative can then be deprotected using potassium trimethylsilanoate in a solvent such as THF to give the desired carboxylic acid. In step B, the carboxylic acid can be converted in situ to the corresponding acid chloride under conditions well known in the art using chloride sources such as oxalyl chloride or thionyl chloride in a solvent such as acetonitrile and adding a catalytic amount of N,N-dimethylformamide, and stirring for about 1.5 hours. The crude acid chloride material is concentrated, slurried in acetonitrile, and added to the aniline that is pre-warmed to about 50° C. in a solvent such as acetonitrile. The product is then isolated and purified using conditions well known in the art. For example, isolation from a basic wash and extraction with DCM followed by chromatography purification provides the compound of Formula Ia.

The following Preparations and Examples further illustrate the invention.

PREPARATION 1

4-Bromo-1-fluoro-2-isopropenyl-benzene

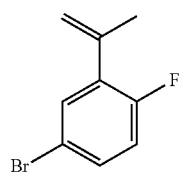

Mix together methyltriphenylphosphonium bromide (276 mmol, 100 g) and THF (1000 mL). Treat with potassium tert-butoxide (276 mmol, 31 g). Stir at room temperature for 1 hour, then add 1-(5-bromo-2-fluoro-phenyl)ethanone (50 g, 230 mmol) as a solution in THF (500 mL) via an addition funnel over about 5 minutes. Stir at room temperature for 3 hours, dilute with EtOAc (1000 ml) and water (500 ml) and separate the layers. Extract the aq. layer with EtOAc (2×250 ml). Combine the organic extracts, wash with brine (500 ml) and dry over MgSO$_4$. Filter the solution and concentrate in vacuo to give the crude product. Dissolve the material in minimal DCM and divide approximately in half. Load each half separately onto a fritted funnel with approximately 50 g of silica gel. Elute with 10% EtOAc/hexanes. Combine the two filtrates and concentrate to give the title compound (43.3 g, 87.4%). $^1$H NMR (CDCl$_3$) δ 2.15 (s, 3H), 5.28 (d, 2H), 6.95 (dd, 1H), 7.34 (m, 1H), 7.46 (dd, 1H). See also US2011/0021520.

PREPARATION 2

(2S)-2-(5-Bromo-2-fluoro-phenyl)propane-1,2-diol

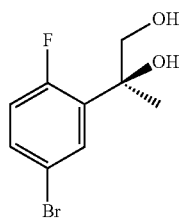

Dissolve 4-bromo-1-fluoro-2-isopropenyl-benzene (22.1 g, 103 mmol) in tert-butyl alcohol (400 mL) and water (400 mL). Cool to 0° C. and add potassium ferricyanide (113 g, 339 mmol), potassium osmate(VI) dihydrate (0.24 g, 0.719 mmol), potassium carbonate (339 mmol, 47.3 g) and (DHQ)$_2$ PHAL (0.84 g, 1.03 mmol). Stir for 18 hours while allowing the reaction to slowly warm to room temperature. Add portion-wise and with care, sodium metabisulfite (60 g, 308 mmol) over about 30-45 minutes, then stir an additional 10 minutes. Dilute with EtOAc (500 ml) and water (100 ml). Separate the layers and extract the aq. layer with EtOAc (2×500 ml). Combine the organic extracts and wash with brine (500 ml). Dry over MgSO$_4$, filter, and concentrate in vacuo to give the title compound (34.5 g, 68% purity, 104%). $^1$H NMR (CDCl$_3$) δ 1.54 (s, 3H), 3.71 (d, 1H), 3.92 (d, 1H), 6.91 (dd, 1H), 7.34 (m, 1H), 7.79 (dd, 1H). See also US2011/0021520.

PREPARATION 3

(2S)-2-(5-Bromo-2-fluoro-phenyl)-2-methyl-oxirane

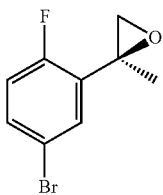

Dissolve (2S)-2-(5-bromo-2-fluoro-phenyl)propane-1,2-diol (25.6 g, 103 mmol) in DCM (700 mL). Add triethylamine (206 mmol, 29 mL). Cool to 0° C. and treat with methanesulfonyl chloride (113 mmol, 9 mL) by syringe addition over several minutes. Stir the solution for 2 hours. Some starting diol may remain in which case add an additional (4.5 mL, 56 mmol) of methanesulfonyl chloride while still at 0° C. Stir another 1 hour, monitoring by LC/MS until conversion to the intermediate mesylate is observed, (ES/MS m/z ($^{79}$Br/$^{81}$Br) 344/346 [M+H$_2$O]$^+$). Pour the reaction into 1 N HCl (500 mL) and extract with DCM (2×400 mL). Combine the organic extracts, wash with NaHCO$_3$(aq) and then with brine. Dry over MgSO$_4$, filter, and concentrate to give the crude mesylate intermediate. Dissolve the residue in MTBE (700 mL) and treat with 1 M sodium hydroxide (aq), (257 mmol, 257 mL). Stir the resulting biphasic reaction vigorously overnight at room temperature. Pour the reaction into NaH$_2$PO$_4$ (aq, 400 mL). Separate the layers and extract the aqueous layer with additional MTBE (2×200 mL). Combine the organic extracts, wash with NaH$_2$PO$_4$ (aq) and then with brine, dry over MgSO$_4$, filter, and concentrate. Purify by silica gel flash chromatography eluting with a gradient of 0-10% EtOAc/hexanes to give the title compound (17.8 g, 70%). $^1$H NMR (CDCl$_3$) δ 1.67 (s, 3H), 2.81 (d, 1H), 2.97 (d, 1H), 6.95 (dd, 1H), 7.38 (m, 1H), 7.56 (dd, 1H). See also US2011/0021520.

PREPARATION 4

(2S)-1-Azido-2-(5-bromo-2-fluoro-phenyl)propan-2-ol

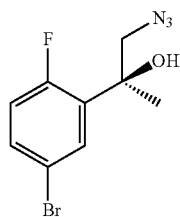

Dissolve (2S)-2-(5-bromo-2-fluoro-phenyl)-2-methyl-oxirane (29.2 g, 119 mmol) in ethanol (450 mL). Add sodium azide (273 mmol, 17.8 g), ammonium chloride (594 mmol, 31.8 g) and 18-crown-6 (119 mmol, 31.4 g). Warm the solution to 84° C. under nitrogen for 5 hours. Vent the reaction head space into a 1 N NaOH solution to capture any NH$_3$ gas that may form in the course of the reaction. Cool the solution to room temperature. Dilute with EtOAc (500 mL) and pour into NaHCO$_3$(aq, 300 mL). Separate the layers and extract the aqueous layer with EtOAc (2×200 mL). Combine the organic extracts, wash with brine, dry over MgSO$_4$, filter, and concentrate to give the title compound (30.9 g, 90% purity, 95%). $^1$H NMR (CDCl$_3$) δ 1.61 (s, 3H), 3.58 (d, 1H), 3.82 (d, 1H), 6.95 (dd, 1H), 7.41 (m, 1H), 7.81 (dd, 1H). See also US2011/0021520.

PREPARATION 5

(2S)-1-Amino-2-(5-bromo-2-fluoro-phenyl)propan-2-ol

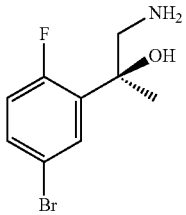

Add a solution of lithium aluminum hydride (2 M in THF, 124 mmol, 62.0 mL) to THF (250 mL) and cool to 0° C. Slowly add via addition funnel, (2S)-1-azido-2-(5-bromo-2-fluoro-phenyl)propan-2-ol (30.9 g, 113 mmol) as a solution in THF (150 mL) over about 1 hour. Stir for 3 hours monitoring by LC/MS. Quench the reaction by the careful addition of water (4.7 ml), 5 M NaOH (4.7 ml) and further water (14 ml). Stir the mixture at room temperature for 2 hours. Add MgSO$_4$ (~3 g), filter, and concentrate to give the title compound (20.98 g, 75.0%). ES/MS m/z ($^{79}$Br/$^{81}$Br) 248/250 [M+H]$^+$ See also US2011/0021520.

PREPARATION 6

N-[(2S)-2-(5-Bromo-2-fluoro-phenyl)-2-hydroxy-propyl]-2-nitro-benzenesulfonamide

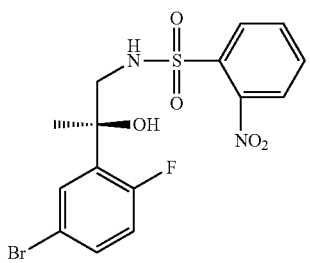

Dissolve (2S)-1-amino-2-(5-bromo-2-fluoro-phenyl)propan-2-ol (20.98 g, 84.57 mmol) in THF (500 mL) and cool to about 0° C. Add 2-nitrobenzenesulfonyl chloride (101.5 mmol, 23.19 g) followed by dropwise addition of NaOH (1 M in water, 93.02 mmol, 93.02 mL) via an addition funnel over 15 minutes. Stir for 5 minutes then warm to room temperature and continue stirring for 4 hours. Dilute with EtOAc (250 mL) and pour into NaH$_2$PO$_4$ (aq, 300 mL). Separate the layers and extract the aqueous layer with EtOAc (2×200 mL). Combine the organic extracts, wash with brine, dry over MgSO$_4$, filter, and concentrate to give the crude product. Purify the residue via silica gel flash chromatography eluting with a gradient of 0-50% EtOAc/hexanes to give the title compound (24.9 g, 68%). ES/MS m/z ($^{79}$Br/$^{81}$Br) 431/433 [M−H]−. See also US2011/0021520.

PREPARATION 7

(2R)-2-(5-Bromo-2-fluoro-phenyl)-2-methyl-1-(2-nitrophenyl)sulfonyl-aziridine

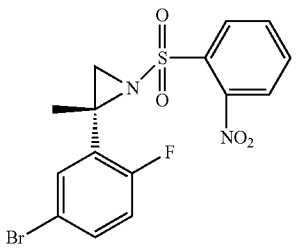 [SMILES: C[C@@]1(c2cc(Br)ccc2F)CN1S(=O)(=O)c1ccccc1[N+](=O)[O-]]

Dissolve N-[(2S)-2-(5-bromo-2-fluoro-phenyl)-2-hydroxy-propyl]-2-nitro-benzenesulfonamide (24.9 g, 57.5 mmol) in DCM (400 mL) and THF (100 mL). Cool to 0° C. Add triphenyl phosphine (86.2 mmol, 22.8 g) and diisopropyl azodicarboxylate (86.2 mmol, 17.8 g) via syringe over ~10 minutes. Stir at room temperature for 24 hours. Pour into NaHCO$_3$(aq. 500 mL) and extract with EtOAc (2×250 mL). Wash the organic extracts with water then with brine. Dry over MgSO$_4$, filter, and concentrate to give the crude product. Purify by silica gel flash chromatography eluting with gradient of 0-50% EtOAc/hexanes to give the title compound (12.7 g, 53.2%). ES/MS m/z ($^{79}$Br/$^{81}$Br) 415/417 [M+H]$^+$. See also US2011/0021520.

PREPARATION 8

Propyl (2R)-3,3,3-trifluoro-2-hydroxy-2-methyl-propanoate

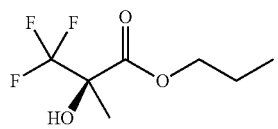

Dissolve (R)-3,3,3-trifluoro-2-hydroxy-2-methylpropionic acid (7.84 g, 48.6 mmol) in 1-propanol (36.7 mL). Add HCl (37 mass % in H$_2$O, 63.2 mmol, 5.2 mL). Heat the solution to 85° C. for 20 hours then cool to room temperature. Dilute with ethyl ether (200 mL) and pour into NaHCO$_3$(aq, 200 mL). Extract the aqueous layer with additional ethyl ether (2×100 mL). Combine the organic extracts, wash with water and then with brine. Dry over MgSO$_4$, filter, and concentrate at room temperature to give the title compound, (7 g, 73%). $^1$H NMR (CDCl$_3$) δ 0.99 (t, 3H), 1.61 (s, 3H), 1.75 (m, 2H), 3.84 (bs, 1H) 4.27 (m, 2H). See also US2011/0021520.

PREPARATION 9

Propyl (2R)-2-[(2S)-2-(5-bromo-2-fluoro-phenyl)-2-[(2-nitrophenyl)sulfonylamino]propoxy]-3,3,3-trifluoro-2-methyl-propanoate

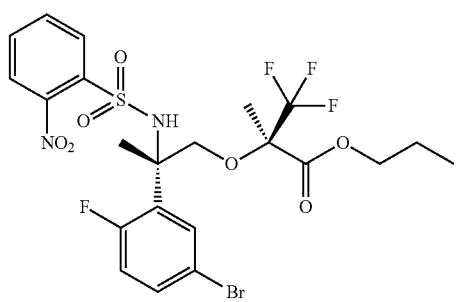 [SMILES: CCCOC(=O)[C@@](C)(OC[C@@](C)(NS(=O)(=O)c1ccccc1[N+](=O)[O-])c1cc(Br)ccc1F)C(F)(F)F]

Dissolve propyl (2R)-3,3,3-trifluoro-2-hydroxy-2-methyl-propanoate (1.566 mmol, 0.3730 g) in N,N-dimethylformamide (5 mL). Add potassium tert-butoxide (1.566 mmol, 0.1774 g) and stir at room temperature for 1 hour. Add (2R)-2-(5-bromo-2-fluoro-phenyl)-2-methyl-1-(2-nitrophenyl)sulfonyl-aziridine (500 mg, 1.204 mmol) as a solution in N,N-dimethylformamide (2.5 mL) and stir at room temperature for 24 hours. Pour into NH$_4$Cl (aq., 150 mL) and extract with EtOAc (3×100 mL). Wash the organic extracts with brine, dry over MgSO$_4$, filter, and concentrate to give the crude product. Purify by silica gel flash chromatography eluting with a gradient of 0-50% THF/hexanes to give the title compound (0.5 g, 70%). ES/MS m/z ($^{79}$Br/$^{81}$Br) 617/619 [M−H]−.

PREPARATION 10

(2R)-2-[(2R)-2-(5-Bromo-2-fluoro-phenyl)-2-[(2-nitrophenyl)sulfonylamino]propoxy]-3,3,3-trifluoro-2-methyl-propanamide

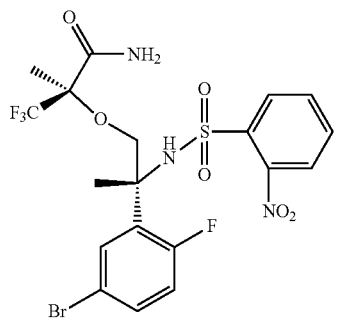 [SMILES: C[C@@](CO[C@](C)(C(N)=O)C(F)(F)F)(NS(=O)(=O)c1ccccc1[N+](=O)[O-])c1cc(Br)ccc1F]

Dissolve propyl (2R)-2-[(2R)-2-(5-bromo-2-fluoro-phenyl)-2-[(2-nitrophenyl)sulfonylamino]propoxy]-3,3,3-trifluoro-2-methyl-propanoate (0.72 g, 1.2 mmol) in 7 M ammoniated MeOH (30 mL). Seal and heat the solution to 60° C. for 18 hours. Concentrate the solution to give the crude product. Purify by silica gel flash chromatography eluting with a gradient of 0-100% EtOAc/hexanes to give the title compound (0.55 g, 82%). ES/MS m/z ($^{79}$Br/$^{81}$Br) 570/572 [M−H]−. See also US2011/0021520.

PREPARATION 11

N-[(1R)-1-(5-Bromo-2-fluoro-phenyl)-2-[(1R)-1-cyano-2,2,2-trifluoro-1-methyl-ethoxy]-1-methyl-ethyl]-2-nitro-benzenesulfonamide

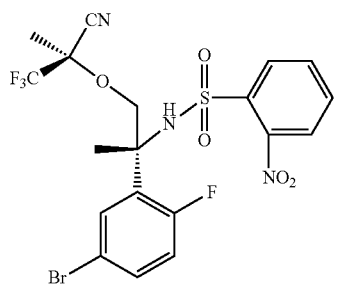 [SMILES: C[C@](C#N)(OC[C@](C)(NS(=O)(=O)c1ccccc1[N+](=O)[O-])c1cc(Br)ccc1F)C(F)(F)F]

Dissolve (2R)-2-[(2R)-2-(5-bromo-2-fluoro-phenyl)-2-[(2-nitrophenyl)sulfonylamino]propoxy]-3,3,3-trifluoro-2-methyl-propanamide (0.65 g, 1.1 mmol) in DCM (10 mL). Cool to 0° C. Add triethylamine (2.8 mmol, 0.40 mL) followed by trifluoroacetic anhydride (1.4 mmol, 0.19 mL). Stir ~10 min at 0° C. and then stir at room temperature for 4 hours. Pour into NaHCO₃(aq) and extract with DCM (2×100 mL). Wash the organic extracts with brine, dry over MgSO₄, filter, and concentrate to give the title compound (590 mg, 94%). ES/MS m/z ($^{79}$Br/$^{81}$Br) 552/554 [M−H]−. See also US2011/0021520.

PREPARATION 12

(3R,6R)-3-(5-Bromo-2-fluoro-phenyl)-3,6-dimethyl-6-(trifluoromethyl)-2H-1,4-oxazin-5-amine

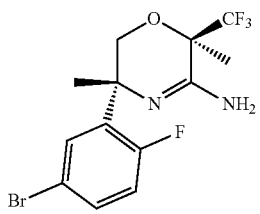 [SMILES: C[C@@]1(c2cc(Br)ccc2F)CO[C@@](C)(C(F)(F)F)C(N)=N1]

Dissolve N-[(1R)-1-(5-bromo-2-fluoro-phenyl)-2-[(1R)-1-cyano-2,2,2-trifluoro-1-methyl-ethoxy]-1-methyl-ethyl]-2-nitro-benzenesulfonamide (2.84 g, 5.12 mmol) in MeOH (51 mL). Add N-Acetyl-L-cysteine (15.4 mmol, 2.51 g) followed by potassium carbonate (15.4 mmol, 2.12 g). Heat the reaction to 80° C. and stir for 24 hours. Cool to room temperature, dilute with EtOAc (100 mL), and pour into NaHCO₃(aq, 100 mL). Extract the aqueous layer with EtOAc (3×100 mL). Wash the combined organic extracts with brine, dry over MgSO4, filter, and concentrate to give the crude product. Purify by silica gel chromatography eluting with a gradient of 0-100% EtOAc/hexanes to give the title compound (1.22 g, 65%). ES/MS m/z ($^{79}$Br/$^{81}$Br) 369/371 [M+H]+. See also US2011/0021520.

PREPARATION 13

(3R,6R)-3-(5-Amino-2-fluoro-phenyl)-3,6-dimethyl-6-(trifluoromethyl)-2H-1,4-oxazin-5-amine

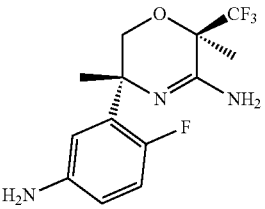 [SMILES: C[C@@]1(c2cc(N)ccc2F)CO[C@@](C)(C(F)(F)F)C(N)=N1]

Scheme 1: Dissolve (3R,6R)-3-(5-bromo-2-fluoro-phenyl)-3,6-dimethyl-6-(trifluoromethyl)-2H-1,4-oxazin-5-amine (300 mg, 0.8126 mmol) in DMSO (9 mL) in a microwave vessel. Add cuprous iodide (0.8126 mmol, 0.1579 g), potassium carbonate (2.438 mmol, 0.3369 g), L-hydroxyproline (1.625 mmol, 0.2131 g), and ammonia (23 mass %) in water (16.25 mmol, 1.34 mL). Seal the microwave vessel and heat via microwave irradiation to 100° C. for 90 minutes. Load the reaction mixture onto a 10 g SCX (ion exchange resin) cartridge. Elute with MeOH (about 20 mL), 1:1 DCM:MeOH. MeOH collecting the eluent as fraction 1, which is discarded. Elute the title product with 7 N NH₃ in MeOH (about 40 mL). Repeat as necessary if product is observed in fraction 1. Concentrate fraction 2 to give the title compound (0.200 g, 80%). ES/MS m/z 306 [M+H]+.

PREPARATION 14

Ethyl 2-[(2,6-dichloro-3-pyridyl)amino]-2-oxo-acetate

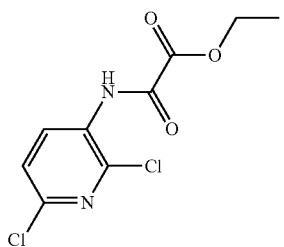 [SMILES: CCOC(=O)C(=O)Nc1ccc(Cl)nc1Cl]

Add ethyl oxalyl chloride (308 g, 2211 mmol) to a solution of 2,6-dichloropyridin-3-amine (300 g, 1840.5 mmol) and triethylamine (321 mL) in THF (3 L) at 0° C. under a nitrogen atmosphere over 45 minutes. Stir at 5° C. for 15 minutes then heat to 20° C. for 30 minutes. If the reaction is incomplete by LCMS, the reaction mixture should be cooled to 10° C. and further charges of triethylamine and ethyl oxalyl chloride should be made until satisfactory conversion is achieved. Once reaction is complete, cool to 10° C. and quench with water (3 L) and stir for 10 minutes. Remove volatiles under reduced pressure and extract the material with EtOAc (3 L). Wash the organic extract with water (1.5 L) and brine (1.5 L), dry over sodium sulfate, filter, and evaporate to dryness to give the title compound as a beige solid (476.8 g, 89%). ES/MS m/z ($^{35}$Cl/$^{37}$Cl) 263.0/265.0/267.0 [M+H]$^+$.

PREPARATION 15

Ethyl 5-chlorothiazolo[5,4-b]pyridine-2-carboxylate

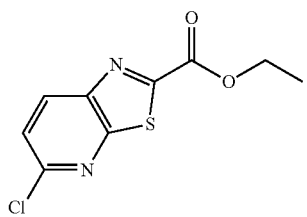

Dissolve ethyl 2-[(2,6-dichloro-3-pyridyl)amino]-2-oxo-acetate (230 g, 874.3 mmol) in acetonitrile (1.1 L), add 2,4-bis(4-methoxyphenyl)-2,4-dithioxo-1,3,2,4-dithiadiphosphetane (Lawesson reagent) (273 g, 654.7 mmol) and heat the resultant mixture to 80° C. for 2 hours. Cool the reaction mixture to 15° C. and remove the solids by filtration, washing the solids with acetonitrile (1.4 L). Cool the filtrate to 15° C. and add cesium carbonate (498.5 g, 1530 mmol) in portions over 30 minutes and then stir at 50° C. for 17 hours or until reaction is complete. Cool the reaction mixture to 15° C. and add water until all the solids are dissolved. Add more water (4.5 L), stir for 15 minutes, and collect the precipitated solid, washing with water (1.5 L). Slurry this solid in water (1.5 L) at ambient temperature for 1 hour, filter, and wash with water (500 mL), collect the solid by filtration, and dry at 40° C. under reduced pressure to give the title compound as a brown solid with about 17% impurity (156.9 g, 61%). ES/MS m/z ($^{35}$Cl/$^{37}$Cl) 242.8/244.8 [M+H]$^+$.

PREPARATION 16

Ethyl 5-cyano[1,3]thiazolo[5,4-b]pyridine-2-carboxylate

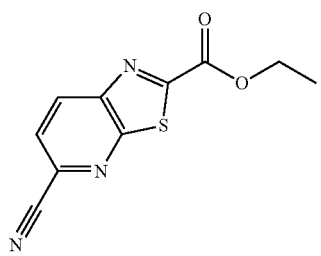 [SMILES: CCOC(=O)c1nc2ccc(C#N)nc2s1]

Scheme 2, step A: Under a nitrogen atmosphere, add 1,4-dioxane (500 mL) and a 50 mM aqueous solution of potassium acetate (490 mL) to ethyl 5-chlorothiazolo[5,4-b]pyridine-2-carboxylate (49.35 g, 193.2 mmol), potassium ferrocyanide trihydrate (36 g, 97.8 mmol), tBuXphos precatalyst generation 3 (4.81 g, 5.9 mmol) and tBuXphos (2.55 g, 5.9 mmol). Heat the resulting mixture to 90° C. for 1.5 hours and then, once reaction is complete, cool to 20° C. and partition between EtOAc (1 L) and saturated aqueous sodium chloride (1 L). Separate the layers, extract the aqueous layer with EtOAc (2×500 mL), dry the combined organic extracts over sodium sulfate, filter, and concentrate under reduced pressure to give a brown solid (50 g). Combine this material with crude material prepared essentially the same to give a total crude material (105.7 g, 73% pure, 331 mmol) and purify the combined material by silica gel flash chromatography eluting with 0%-20% EtOAc in DCM to give the title compound as a tan solid with a combined yield (63.4 g, 54%). ES/MS m/z 234.0 (M+H). Adapted from conditions described by Senecal et al, *Angew. Chem. Int. Ed.,* 2013, 52, 10035-10039.

PREPARATION 17

5-Cyano[1,3]thiazolo[5,4-b]pyridine-2-carboxylic Acid

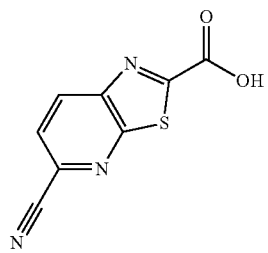 [SMILES: N#Cc1ccc2nc(C(=O)O)sc2n1]

Scheme 2, step A: Dissolve ethyl 5-cyanothiazolo[5,4-b]pyridine-2-carboxylate (69.0 g, 287 mmol) in anhydrous THF (1.4 L) and cool the mixture to an internal temperature of 10° C. Add potassium trimethylsilanoate (51.2 g, 359 mmol) portionwise maintaining the internal temperature below 16° C. and stir the mixture at ambient temperature for 1.5 hours. Collect the solids by filtration, washing with THF (500 mL), and dry under a stream of nitrogen. Dissolve the solid in 1:1 THF/water (1200 mL) and acidify using 2 N aqueous hydrochloric acid (143 mL, 286 mmol). Remove the organic solvent under reduced pressure and cool the remaining aqueous mixture in an ice-water bath. Collect the solids by filtration and dry under vacuum in a dessicator to obtain the title compound as a light orange powder (57.2 g, 92%). ES/MS m/z 160.0 (M–CO$_2$H).

Example 1

N-[3-[(3R,6R)-5-Amino-3,6-dimethyl-6-(trifluoromethyl)-2H-1,4-oxazin-3-yl]-4-fluoro-phenyl]-5-cyano-thiazolo[5,4-b]pyridine-2-carboxamide

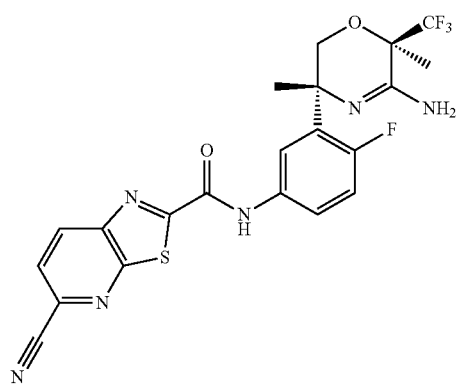 [SMILES: C[C@@]1(c2cc(NC(=O)c3nc4ccc(C#N)nc4s3)ccc2F)CO[C@@](C)(C(F)(F)F)C(N)=N1]

Scheme 2, step B: Mix together 5-cyanothiazolo[5,4-b] pyridine-2-carboxylic acid (0.1277 mmol, 0.02621 g) in acetonitrile (4 mL). Add N,N-dimethylformamide (0.00836 mL) followed by oxalyl chloride (0.1277 mmol, 0.01108 mL). Stir the slurry at room temperature for 1.5 hours. In a separate vessel, dissolve (3R,6R)-3-(5-amino-2-fluoro-phenyl)-3,6-dimethyl-6-(trifluoromethyl)-2H-1,4-oxazin-5-amine (30 mg, 0.09826 mmol) in acetonitrile (4 mL, 76.3 mmol, 3.13 g, 4 mL, 100 mass %) and warm this solution to 50° C. Concentrate the acid chloride mixture to give the crude acid chloride which is re-slurried in acetonitrile (4 mL). Add this acid chloride mixture to the aniline solution while still at 50° C. and stir for 18 hours. Cool to room temperature and pour into NaHCO$_3$ (aq). Extract with DCM (3×75 mL), wash the organic extracts with brine, and concentrate the solution to give the crude product. Purify by silica gel flash chromatography eluting with a gradient of 0-10% (7 N NH$_3$ in MeOH)/DCM to give the title compound (26 mg, 53%). ES/MS m/z: 493[M+H]$^+$.

In Vitro Assay Procedures:

To assess selectivity of BACE1 over BACE2, the test compound is evaluated in FRET assays using specific substrates for BACE1 and BACE2 as described below. For in vitro enzymatic and cellular assays, the test compound is prepared in DMSO to make up a 10 mM stock solution. The stock solution is serially diluted in DMSO to obtain a ten-point dilution curve with final compound concentrations ranging from 10 µM to 0.05 nM in a 96-well round-bottom plate before conducting the in vitro enzymatic and whole cell assays.

In Vitro Protease Inhibition Assays

Expression of huBACE1:Fc and huBACE2:Fc

Human BACE1 (accession number: AF190725) and human BACE2 (accession number: AF 204944) are cloned from total brain cDNA by RT-PCR. The nucleotide sequences corresponding to amino acid sequences #1 to 460 are inserted into the cDNA encoding human IgG$_1$ (Fc) polypeptide (Vassar et al., Science, 286, 735-742 (1999)). This fusion protein of BACE1(1-460) or BACE2(1-460) and human Fc, named huBACE1:Fc and huBACE2:Fc respectively, are constructed in the pJB02 vector. Human BACE1 (1-460):Fc (huBACE1:Fc) and human BACE2(1-460):Fc (huBACE2:Fc) are transiently expressed in HEK293 cells. cDNA (250 µg) of each construct are mixed with Fugene 6 and added to 1 liter HEK293 cells. Four days after the transfection, conditioned media are harvested for purification. huBACE1:Fc and huBACE2:Fc are purified by Protein A chromatography as described below. The enzymes are stored at −80° C. in small aliquots. (See Yang, et. al., J. Neurochemistry, 21(6) 1249-59 (2004).

Purification of huBACE1:Fc and huBACE2:Fc

Conditioned media of HEK293 cells transiently transfected with huBACE1:Fc or huBACE2:Fc cDNA are collected. Cell debris is removed by filtering the conditioned media through 0.22 µm sterile filter. Protein A-agarose (5 ml) (bed volume) is added to conditioned media (4 liter). This mixture is gently stirred overnight at 4° C. The Protein A-agarose resin is collected and packed into a low-pressure chromatography column. The column is washed with 20× bed volumes of PBS at a flow rate 20 ml per hour. Bound huBACE1:Fc or huBACE2:Fc protein is eluted with 50 mM acetic acid, pH 3.6, at flow rate 20 ml per hour. Fractions (1 ml) of eluent are neutralized immediately with ammonium acetate (0.5 ml, 200 mM), pH 6.5. The purity of the final product is assessed by electrophoresis in 4-20% Tris-Glycine SDS-PAGE. The enzyme is stored at −80° C. in small aliquots.

BACE1 FRET Assay

Serial dilutions of the test compound are prepared as described above. The compound is further diluted 20× in KH$_2$PO$_4$ buffer. Each dilution (10 µL) is added to each well on row A to H of a corresponding low protein binding black plate containing the reaction mixture (25 µL of 50 mM KH$_2$PO$_4$, pH 4.6, 1 mM TRITON® X-100, 1 mg/mL BSA, and 15 µM of FRET substrate based upon the sequence of APP) (See Yang, et. al., J. Neurochemistry, 91(6) 1249-59 (2004)). The content is mixed well on a plate shaker for 10 minutes. Human BACE1(1-460):Fc (15 µL of 200 pM) (See Vasser, et al., Science, 286, 735-741 (1999)) in the KH$_2$PO$_4$ buffer is added to the plate containing substrate and the test compound to initiate the reaction. The RFU of the mixture at time 0 is recorded at excitation wavelength 355 nm and emission wavelength 460 nm, after brief mixing on a plate shaker. The reaction plate is covered with aluminum foil and kept in a dark humidified oven at room temperature for 16 to 24 hours. The RFU at the end of incubation is recorded with the same excitation and emission settings used at time 0. The difference of the RFU at time 0 and the end of incubation is representative of the activity of BACE1 under the compound treatment. RFU differences are plotted versus inhibitor concentration and a curve is fitted with a four-parameter logistic equation to obtain the $IC_{50}$ value. (May, et al., *Journal of Neuroscience,* 31, 16507-16516 (2011)).

The compound of Example 1 is tested essentially as described above and exhibits an $IC_{50}$ for BACE1 of 8.18 nM±1.86, n=13 (Mean±standard deviation of the mean). This data demonstrates that the compound of Example 1 inhibits purified recombinant BACE1 enzyme activity in vitro.

BACE2 TMEM27 FRET Assay

Serial dilutions of test compound are prepared as described above. Compounds are further diluted 20× in $KH_2PO_4$ buffer. Each dilution (ten μL) is added to each well on row A to H of a corresponding low protein binding black plate containing the reaction mixture (25 μL of 50 mM $KH_2PO_4$, pH 4.6, 1 mM TRITON® X-100, 1 mg/mL BSA, and 5 μM of TMEM FRET substrate) (dabcyl-QTLE-FLKIPS-LucY, WO 2010063640 A1)). Fifteen μL of twenty μM human BACE2 (1-460):Fc (See Vasser, et al., *Science,* 286. 735-741 (1999)) in $KH_2PO_4$ buffer is then added to the plate containing substrate and test compounds to initiate the reaction. The content is mixed well on a plate shaker for 10 minutes. The RFU of the mixture at time 0 is recorded at excitation wavelength 430 nm and emission wavelength 535 nm. The reaction plate is covered with aluminum foil and kept in a dark humidified oven at room temperature for 16 to 24 h. The RFU at the end of incubation is recorded with the same excitation and emission settings used at time 0. The difference of the RFU at time 0 and the end of incubation is representative of the activity of BACE2 under the compound treatment. RFU differences are plotted versus inhibitor concentration and a curve is fitted with a four-parameter logistic equation to obtain the $IC_{50}$ values. (May, et al., *Journal of Neuroscience,* 31, 16507-16516 (2011)).

The compound of Example 1 is tested essentially as described above and exhibits a BACE2 $IC_{50}$ of 446 nM±92, n=6 (Mean±standard deviation of the mean). The ratio of BACE1 (FRET $IC_{50}$ enzyme assay) to BACE2 (TMEM27 LucY FRET assay) is approximately 50-fold, indicating functional selectivity for inhibiting the BACE1 enzyme. The data set forth above demonstrates that the compound of Example 1 is selective for BACE1 over BACE2.

SH-SY5YAPP695Wt Whole Cell Assay

The routine whole cell assay for the measurement of inhibition of BACE1 activity utilizes the human neuroblastoma cell line SH-SY5Y (ATCC Accession No. CRL2266) stably expressing a human APP695Wt cDNA. Cells are routinely used up to passage number 6 and then discarded.

SH-SY5YAPP695Wt cells are plated in 96 well tissue culture plates at $5.0 \times 10^4$ cells/well in 200 μL culture media (50% MEM/EBSS and Ham's F12, 1× each sodium pyruvate, non-essential amino acids and $NaHCO_3$ containing 10% FBS). The following day, media is removed from the cells, fresh media added then incubated at 37° C. for 24 hours in the presenceabsence of test compound at the desired concentration range.

At the end of the incubation, conditioned media are analyzed for evidence of beta-secretase activity by analysis of Abeta peptides 1-40 and 1-42 by specific sandwich ELISAs. To measure these specific isoforms of Abeta, monoclonal 2G3 is used as a capture antibody for Abeta 1-40 and monoclonal 21F12 as a capture antibody for Abeta 1-42. Both Abeta 1-40 and Abeta 1-42 ELISAs use biotinylated 3D6 as the reporting antibody (for description of antibodies, see Johnson-Wood, et al., *Proc. Natl. Acad. Sci. USA* 94, 1550-1555 (1997)). The concentration of Abeta released in the conditioned media following the compound treatment corresponds to the activity of BACE1 under such conditions. The 10-point inhibition curve is plotted and fitted with the four-parameter logistic equation to obtain the $IC_{50}$ values for the Abeta-lowering effect.

The compound of Example 1 is tested essentially as described above and exhibits an $IC_{50}$ of 1.88 nM±0.17, n=3 for SH-SY5YAPP695Wt A-beta (1-40) ELISA and an $IC_{50}$ of 3.55 nM±0.88, n=3 for SH-SY5YAPP695Wt A-beta (1-42) ELISA (Mean±standard deviation of the mean). The data set forth above demonstrates that the compound of Example 1 inhibits BACE1 in the whole cell assay.

These studies show that compounds of the present invention inhibit BACE1 and are, therefore, useful in reducing Abeta levels.

We claim:
1. A compound of the formula:

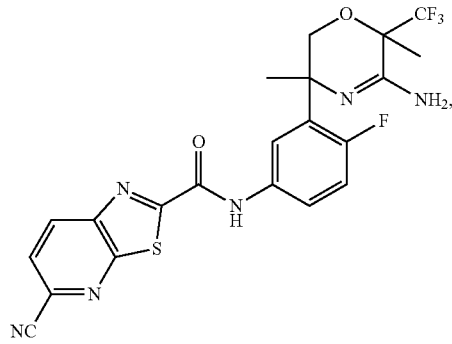 [SMILES: CC1(c2cc(NC(=O)c3nc4ccc(C#N)nc4s3)ccc2F)COC(C)(C(F)(F)F)C(N)=N1]

or a pharmaceutically acceptable salt thereof.

2. The compound or salt according to claim 1 wherein the methyl at position 3 is in the cis configuration relative to the trifluoromethyl at position 6 on the oxazine ring:

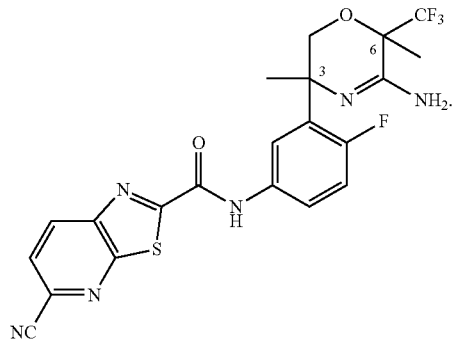 [SMILES: CC1(c2cc(NC(=O)c3nc4ccc(C#N)nc4s3)ccc2F)COC(C)(C(F)(F)F)C(N)=N1]

3. A compound which is N-[3-[(3R,6R)-5-amino-3,6-dimethyl-6-(trifluoromethyl)-2H-1,4-oxazin-3-yl]-4-fluorophenyl]-5-cyano-thiazolo[5,4-b]pyridine-2-carboxamide, or a pharmaceutically acceptable salt thereof.

4. A method of treating Alzheimer's disease in a patient, comprising administering to a patient in need of such treatment an effective amount of a compound according to claim 1, or a pharmaceutically acceptable salt thereof.

5. A method of preventing the progression of mild cognitive impairment to Alzheimer's disease in a patient, comprising administering to a patient in need of such treatment an effective amount of a compound according to claim 1, or a pharmaceutically acceptable salt thereof.

6. A pharmaceutical composition, comprising a compound or a pharmaceutically acceptable salt thereof according to claim 1, with one or more pharmaceutically acceptable carriers, diluents, or excipients.

7. A process for preparing a pharmaceutical composition, comprising admixing a compound or a pharmaceutically acceptable salt thereof according to claim 1 with one or more pharmaceutically acceptable carriers, diluents, or excipients.

8. A method of treating Alzheimer's disease in a patient, comprising administering to a patient in need of such treatment an effective amount of a compound according to claim 3, or a pharmaceutically acceptable salt thereof.

9. A method of preventing the progression of mild cognitive impairment to Alzheimer's disease in a patient, comprising administering to a patient in need of such treatment an effective amount of a compound according to claim 3, or a pharmaceutically acceptable salt thereof.

10. A pharmaceutical composition, comprising a compound or a pharmaceutically acceptable salt thereof according to claim 3 with one or more pharmaceutically acceptable carriers, diluents, or excipients.

* * * * *